United States Patent [19]

Leach

[11] 3,965,045

[45] June 22, 1976

[54] IRON CATALYST

[75] Inventor: Bruce E. Leach, Ponca City, Okla.

[73] Assignee: Continental Oil Company, Ponca City, Okla.

[22] Filed: Feb. 20, 1975

[21] Appl. No.: 551,573

[52] U.S. Cl................. 252/466 J; 260/449.6
[51] Int. Cl.².............. B01J 21/04; B01J 21/74
[58] Field of Search........... 252/466 J; 260/449.6

[56] References Cited
UNITED STATES PATENTS
2,700,676   1/1955   McGrath.................. 260/450

Primary Examiner—W. J. Shine
Attorney, Agent, or Firm—Cortlan R. Schupbach, Jr.

[57] ABSTRACT

An improved iron catalyst is provided which is useful in catalytically synthesizing hydrocarbons from carbon monoxide and hydrogen. The catalyst comprises a calcined and reduced mixture of magnetite and alumina derived from water hydrolysis of aluminum alkoxides wherein at least 70 wt % of the magnetite has been reduced and the alumina is in the gamma form.

16 Claims, No Drawings

IRON CATALYST

This invention relates to a novel iron catalyst, a method of preparing such catalyst and the use of such catalyst in synthesizing organic compounds from hydrogen and carbon monoxide.

Syntheses of organic compounds from hydrogen and carbon monoxide in the presence of a catalyst are known in the art and commonly referred to as Fischer-Tropsch syntheses. In general, these syntheses involve the reaction of hydrogen and carbon monoxide in the presence of a metal or an oxide of a metal selected from Group VIII of the Periodic Table as a catalyst at elevated pressures and temperatures. Particularly suitable catalysts for these syntheses are derived from iron compounds as described in U.S. Pat. No. 2,543,327 and U.S. Pat. No. 2,944,988. While the catalysts described in these patents are effective in synthesizing organic compounds it is desirable to improve on such catalysts.

In accordance with this invention it has been found that improved iron catalysts may be prepared by calcining and then reducing a mixture of magnetite and an alumina which has been obtained by water hydrolysis of aluminum alkoxides wherein the calcination is carried out at temperatures in the range of about 650°C to a temperature below that at which the gamma form of alumina is converted to the delta form, nominally about 850°C, and reduction is carried out to the extent that at least 70 wt % of the magnetite is reduced. Iron catalysts prepared with this particular alumina under the particular calcination conditions have been found to produce several advantageous results in Fischer-Tropsch synthesis compared to iron catalysts conventionally prepared with alumina derived from other sources. Among these advantages are included high conversion of carbon monoxide to organic compounds, lower carbon dioxide formation and higher catalyst activity. In addition, it has been found that the organic compounds formed have a higher olefin content.

The magnetite employed in preparing the catalysts of the invention may be naturally occurring magnetite ore or formed by fusion of iron ores, e.g. mill scale. Examples of suitable naturally occurring ores are Allenwood ore native to New Jersey and ore from the Ermelo district of the Republic of South Africa.

The alumina employed in the catalysts is that which is obtained by the water hydrolysis of aluminum alkoxides. A typical technique for obtaining alumina in this manner is described in U.S. Pat. No. 3,419,352 as well as in other prior art literature. Generally, such alumina is produced by hydrolyzing aluminum alkoxides, such as those obtained from the well-known Ziegler growth process, with an excess of water to form an alcoholic organic portion and an aqueous alumina portion, thereafter separating the two portions and mildly drying the aqueous alumina portion to obtain the alumina. The alumina thus obtained is in the alpha monohydrate form and is in a finely divided state. Upon heating to successive elevated temperatures, the alpha monohydrate form is converted to gamma alumina at about 500°C. The gamma form is converted to the delta form at about 850°C which in turn goes to the theta form and finally the alpha form at even higher temperatures. All of this is described in published Alumina Properties by J. W. Newsome et al, Alcoa Research Laboratories, Technical Paper No. 10, 2nd Revision (1960), published by Aluminum Company of America, particularly at page 46.

For purposes of this invention, it is also believed essential that prior to calcining the alumina be in the alpha monohydrate form or gamma form. In the former case the alpha monohydrate is converted to the gamma form upon calcining so that regardless of which of the two forms are initially employed in preparing the catalyst it is the gamm form which ultimately is the alumina present in the final catlayst. As noted hereinafter, care must be exercised in calcining the catalyst so as to avoid those high temperatures whereat any significant quantity of the gamma alumina may be converted to the delta form.

Thus, from the above discussion it should be understood that the alumina employed in the invention must be derived from water hydrolysis of aluminum alkoxides and must also be in either the alpha monohydrate form or gamma form.

In preparing the catalysts of the invention it is advantageous to initially comminute the magnetite, if necessary, to a desired particle size distribution in which it will be subsequently employed in catalyzing Fischer-Tropsch reactions. For example, in fixed-bed catalyst operatiosn the particle size will usually be greater than about 100 microns with the particles advantageously of an irregular shape. For fluidized bed or streaming-circulation of catalysts the particle size will usually be greater than about 10 microns but but less than about 500 microns. These sizes are, of course, typical and may vary depending upon the particular system being employed and can be determined by those skilled in the art for any given operation.

In any event, the particulate magnetitie is mixed with the alumina, which is in a finely divided state, and the mixture is calcined for at least one-half hour at temperatures in the range of about 650°C up to a temperature below that at which the gamma alumina becomes converted to delta alumina to any significant extent. According to *Alumina Properties*, supra, the nominal temperature at which gamma alumina is converted to delta alumina is about 850°C temperatures of from 700°C to 850°C are preferred. The pressures at which calcination is conducted are not critical as one skilled in the art will understand. The time of calcination should be at least one-half hour as shorter times may result in a catalyst which suffers from undue alumina removal through attrition. On the other hand, calcination may be conducted for periods of time much greater than one-half hour as the principal consideration is merely one of practicality.

The amount of the previously described alumina employed with the magnetite is in the range of about 0.1 to 5 weight percent based on the magnetite, preferably in the range of about 2 to 4 weight percent and most preferably in the range of about 2.5 to 3.5 weight percent. Amounts below that specified above result in catalysts having unduly low activity while amounts of alumina above about 5 weight percent apparently result in some embrittlement of the catalyst and excessive fines are encountered in use.

After calcination the catalyst is subjected to reduction to increase its activity. The reduction is carried out using a reducing gas, such as hydrogen or hydrogen containing carbon monoxide or other suitable gasiform reducing agents, at temperatures in the range of about 200° to 600°C, preferably 300° to 500°C and more preferably 350° to 500°C. While the reduction can suitably be carried out at atmospheric pressure it may be accelerated with application of increased pressures. In general, the reduction will be conducted at pressures of atmospheric up to about 75 atmospheres.

The reduction step is carried out for a sufficient period of time to reduce at least about 70 weight percent of the magnetite, preferably at least about 90 weight percent. The extent of reduction can be determined during the reducing process by the amount of water removed.

The thus-formed catalyst is then ready for use in conducting Fischer-Tropsch reactions. In these reactions, hydrogen and carbon monoxide are reacted in the presence of the catalyst to form hydrocarbons. As is known in the art, when employing a freshly formed catalyst, such as described above, in these reactions there is encountered an initial induction or conditioning period during which time carbiding of the catalyst occurs. Under conditions of the reactions the rate of carbon deposition on the catalyst is much greater during carbiding than after the catalyst has become carbided. In this regard the catalyst of the present invention shows improvement over other closely related prior art catalysts since the period required for carbiding of the present catalyst is shorter than that for the prior art catalysts and, thus, it would be expected that the resulting total carbon deposition is less.

Carbiding of the catalysts may be accomplished, alternatively, as a preconditioning step wherein conditions can be employed which further minimize carbon deposition. This preconditioning step may be integrated with the Fischer-Tropsch type reactions by simply adjusting the conditions of the reaction. For example, it is preferred to onduct the preconditioning step by passing a hydrogen/carbon monoxide mixture having a mole ratio of $H_2/CO$ of at least 3/1 over the catalyst at temperatures in the range of about 200° to 350°C, preferably about 250° to 325°C, at pressures in the range of about 2 to 30 atmospheres. Pressure less than 2 atmospheres result in unduly slow carbiding while pressures above about 30 atmospheres produce little benefits. At these relatively mild conditions carbiding proceeds readily yet the rate of carbon deposition is lower. By monitoring the effluent gas stream, as by gas chromatography, it can be ascertained when carbiding is essentially complete by noting when the product composition ceases to change rapidly. At this stage, if the preconditioning is integrated with a Fischer-Tropsch reaction, it is merely necessary to adjust flow rates and conditions as desired to proceed with the Fischer-Tropsch reaction. Of course, as will be readily recognizied, this preconditioning step may be conducted separately from any ultimate use of the catalyst in Fischer-Tropsch reactions.

Promoters can also be employed in the above described catalyst as desired. Included as such promoters are various metals and silicon and their compounds such as oxides, nitrates, chlorides, carbonates, hydroxides and organic compounds. Alkali metal compounds are particularly suiable. Typical examples are Co, Ni, Ti, Si, Al, $TiO_2$, CuO, $SiO_2$, $K_2O$, CoO, $CsO_3$, MgO, MnO, $ThO_2$, $MoO_3$, $K_2CO_3$, $Al(COOH)_3$, $Al(NO_3)_3$, $Mn(NO_3)_2$, ZnO, $Cs(OH)_4$, KOH, $Co(NO_3)_2$, $H_2MoO_4$, KCl, $SiCl_4$, $AlCl_3$, $H_2SiO_3$, $Rb_2CO_3$, $CsCO_3$, and the like. Alumina derived from sources other than water hydrolysis of aluminum alkoxides may also be included and in many instances naturally occurring alumina is already present to some extent in the magnetite. Normally additional amounts of such alumina will not be introduced to the catalyst in view of the specific alumina already present in accordance with the invention.

By non-alkali metal promoters it is meant non-alkali metals and their compounds as described above. Similarly, alkali metal promoters is used to indicate both alkali metals and their compounds.

The amount of promoter employed can vary considerably depending on the results desired. Generally, amounts in the range of about 0.01 to 10 weight percent based on the catalyst will be suitable.

Non-alkali metal promoters should be added to the catalyst prior to calcination whereas the alkali metal promoters may be added at any time prior to substantial reduction of the catalyst, e.g. prior to calcination, prior to reduction or sometime during reduction.

Application or introduction of the promoters to the catalyst may be performed in any suitable manner as is known in the art. They may be simply added as is or by impregnation from aqueous alcoholic solutions. Such solutions may be sprayed on or simply trickled over the catalyst. Applying vacuum to the catalyst may aid in the impregnation. Certain detergents or wetting agents may be advantageously used to improve impregnation.

Of all of the various promoters which may be used potassium and its compounds are preferred such as potassium carbonate and potassium hydroxide. In addition to promoting catalysis of the Fischer-Tropsch reactions potassium also has the effect of increasing the rate of carbiding.

As indicated hereinbefore, the catalysts of this invention are useful in conducting Fischer-Tropsch syntheses to produce hydrocarbons. In these syntheses the essential components of the feedstock are hydrogen and carbon monoxide and a typical synthesis in which the catalyst of the invention can be employed is described hereinafter. However, it should be understood that the catalyst may be used in any Fischer-Tropsch synthesis.

In general, the mole ratio of hydrogen to carbon monoxide in the feedstock should be at least 1/1, and preferably at least 1.5/1. Low amounts of hydrogen decrease the reaction rate and, perhaps more importantly, tend to result in some disassociation of the carbon monoxide to carbon dioxide and elemental carbon, which, as mentioned before, should be minimized as it deposits on the interior of the reaction zone and on the catalyst. This results in decreased heat transfer, a factor which may be significant in view of the exothermic nature of the reaction, and in decreased activity of the catalyst. As the mole ratio of hydrogen to carbon monoxide increases the rate of reaction generally increases up to a point after which it either remains somewhat constant or even tapers off. In addition, high amounts of hydrogen generally tend to result in lower average molecular weight products with saturated compounds favored over unsaturated compounds. Another factor to be considered with high amounts of hydrogen is that the unconsumed hydrogen must be carried through and subsequently be separated in the process, even though it may be recycled. Considering all of these aspects, it is generally desired to operate the process with a mole ratio of hydrogen to carbon monoxide of less than about 5/1, and preferably in the range of about 2/1 to 4/1.

A portion of the hydrogen and carbon monoxide to the reaction may be provided by introducing water (steam) and carbon dioxide as part of the feedstock.

Under conditions of the reaction, the well-known water gas shift takes place to some extent as follows:

$$H_2O + CO \rightleftharpoons H_2 + CO_2$$

However, the reversible nature of the reaction should be taken into consideration in determining the amounts of water or carbon monoxide to be included in the feedstock.

It is further mentioned that the hydrogen-carbon monoxide feedstock can contain other materials such as methane or higher hydrocarbons or oxygenated hydrocarbons or inert materials such as nitrogen, argon, and the like. In fact, for reactor control, it may be desirable to recycle a portion of the effluent or part of the effluent from the reaction zone after being cooled. When other materials are present, it is generally desirable to maintain the hydrogen/carbon monoxide concentration as high as possible consistent with maintaining control over the reaction zone.

Sulfur compounds such as $H_2S$ or COS in the feedstock are undesirable as they tend to deactivate the catalyst. Thus, if the feedstock contains more than tolerable traces of such sulfur compounds, it may become necessary to replace the catalyst more often than would normally be acceptable.

A particularly suitable source of a feedstock for the Fischer-Tropsch reactions is the effluent from gasification of coal with steam and oxygen which has been suitably treated to remove sulfur compounds as known in the art. Such effluents contain considerable quantities of hydrogen and carbon monoxide along with some methane, carbon dioxide, water and possibly higher hydrocarbons. If the mole ratio of hydrogen to carbon monoxide is lower than that desired, the effluent may be subjected to a water gas shift reaction to increase the ratio to the desired value. It may also be adjusted from external sources of hydrogen. While not necessarily essential, the gasification effluent may also be subjected to a separation step; e.g., cryogenic separation, to remove most of the carbon dioxide, water, methane, and higher hydrocarbons to provide a feedstock consisting essentially of only hydrogen and carbon monoxide.

The Fischer-Tropsch reaction may be conducted at temperatures in the range of about 150°C to about 450°C. Lower temperatures tend to result in higher molecular weight products which may cause fouling of the catalyst or reaction zone. On the other hand, higher temperatures tend to result in production of increased carbon which likewise may cause catalyst fouling. Preferred temperatures are in the range of about 200°C to 400°C with the most preferred temperature ranging from about 250°C to 350°C.

Pressures as low as atmospheric pressure may be employed but the reaction rate is relatively slow at low pressures. Higher pressures may also be used with the primary considerations being equipment design, possible reactor and catalyst fouling due to the fact that higher pressures tend to result in higher molecular weight products, and reaction control since increased pressure increases the reaction rate. Generally, pressures in the range of 5 to 75 atmospheres [gauge] will be used, preferably 10 to 30 atmospheres [gauge].

The Fischer-Tropsch reaction may be conducted in a zone containing the catalyst as a conventional fixed bed or a fluidized (fixed or entrained types) bed. Normally, a fluidized bed is preferred. Space velocities in the range of about 500 to 5000 volumes of feedstock/volume of catalyst/hour at standard temperature and pressure conditions may be used, preferably in the range of about 3000 to 10000 V/V/hr STP.

The product effluent from the Fischer-Tropsch reaction contains hydrocarbons and a minor amount of oxygenated hydrocarbons in addition to carbon monoxide, hydrogen, carbon dioxide and water. The desired products may be easily recovered from the effluent with techniques known in the art. A convenient recovery system involves rapidly cooling the product mixture and then processing the cooled mixture through a series of low-temperature fractional distillation columns. Hydrogen along with carbon monoxide, carbon dioxide, and water are first removed and may be recycled to the reaction with or without further separation. The next component which may be separated is methane for possible utilization as a synthetic natural gas component. Ethylene, ethane, propylene, propane, etc, may then be sequentially recovered or recovered in combination as desired.

The following examples will serve to further illustrate the invention.

EXAMPLE 1 (BEL-3193-79)

A catalyst in accordance with the invention was prepared by comminuting mill scale (obtained from Armco Steel Corporation, Sand Springs, Oklahoma) in a roller mill until the particle size was less than about 100 mesh (Tyler). By sieving, the 100 to 400 mesh mill scale was separated. A typical analysis of this mill scale (magnetite) indicated the major impurities to be about 0.17 wt % K, 0.17 wt % Ca, 0.1 wt % Cu, 0.1 wt % Cr, 0.07 wt % Mn, and about 0.2 wt % Si.

A commercially available alumina derived from water hydrolysis of aluminum alkoxides in the alpha monohydrate form (Conoco DISPAL M) was slurried with additional water and combined with a quantity of the above mill scale so as to form a homogeneous mixture of mill scale and the alumina wherein the amount of alumina was about 3 wt % based on the mill scale. The mixture was dried to a visible dryness and calcined at about 800°C for 2–3 hours during which time the alpha monohydrate alumina was converted to gamma alumina.

The calcined mixture was then reduced with hydrogen at about 450°C and about 9 ½ atmospheres until about 75–80 wt % of the magnetite was reduced as evidenced by near cessation of water evolution. The resulting catalyst was then suitable for use in catalyzing Fischer-Tropsch reactions.

EXAMPLE 2

The catalyst prepared in Example 1 was compared with a catalyst prepared in the same manner except that the alumina employed was a commercial alumina derived from a sodium aluminate process (Alcoa H151). The comparison of the catalysts was on a basis of time required for carbiding. As indicated earlier herein, carbiding of the catalyst may be accomplished as a preconditioning step or it will inherently occur during the initial stages of a Fischer-Tropsch reaction when using a freshly formed catalyst without preconditioning. In either case it is desirable for carbiding to occur in as short a time period as possible. In the comparison of the two catalysts, carbiding was essentially evaluated as a preconditioning step. In this regard, each catalyst (600 cc) was charged to a fluid bed reactor and separate streams of $H_2$ and CO were flowed therethrough at about 3.7 atmospheres.

Hydrogen was introduced at a constant 1170 l/hr (STP) which was sufficient to maintain the catalyst in a fluidized condition. CO was controllably introduced so as to maintain the temperature between 350°–400°C. Carbiding of the catalyst was considered substantially completed when the CO rate reached at least about 250 l/hr (STP) with no corresponding substantial increase in temperature (essentially a steady-state at that flow rate). The time for this to occur was noted for each catalyst.

For the catalyst of the invention employing an alumina derived from water hydrolysis of aluminum alkoxides and subsequently converted to the gamma form the time for carbiding was about nine (9) hours. For the catalyst employing an alumina derived from a sodium aluminate process the peconditioning was continued for about ninety (90) hours and still the catalyst had not reached the same degree of carbiding as the catalyst of the invention.

EXAMPLE 3

A calcined catalyst in accordance with the invention was prepared as described in Example 1. An aqueous solution of potassium carbonate was added to the calcined catalyst in an amount sufficient to provide 0.13 wt % potassium, based on the total catalyst, and the resulting catalyst was dried to a visible dryness followed by reduction with flowing hydrogen at temperatures in the range of about 400° to 475°C and about 9 ½ atmospheres until about 75–80 wt % of the magnetite and potassium carbonate were reduced as evidenced by near cessation of water evolution.

The resulting catalyst containing the potassium promoter was charged (600 cc) to a 2 ½-inch laboratory fluid bed reactor and a Fischer-Tropsch reaction was conducted by introducing hydrogen at 1,170 l/hr (STP) and carbon monoxide at 243 l/hr (STP), an $H_2/CO$ mole ratio of about 4.8/1; and maintaining the pressure at about 4-6 atmospheres and temperatures in the range of 300°–350°C. The effluent from the reactor was analyzed at the end of about 15 hours of operation. Hydrocarbon analysis was with a poropak Q column and flame ionization detector. $CO_2$, CO and $CH_4$ were determined with a thermal conductivity unit using a molecular sieve column for $CH_4$ and CO and a poropak Q column for $CO_2$ and $CH_4$.

For comparison, another catalyst was prepared and evaluated in a Fischer-Tropsch reaction as described above with the exceptions of employing a commercial alumina derived from a sodium aluminate process (Kaiser KCSA) and the potassium content being about 0.12 wt % based on the total catalyst.

The results obtained for each catalyst are tabulated in the following table:

Table A

| Catalyst | 1[a] | 2[b] |
|---|---|---|
| Total Carbon Deposition (wt %) | 10.6 | 15.3 |
| Effluent Composition (wt %) | | |
| CO | 3.7 | 12.5 |
| $CO_2$ | 35.3 | 43.3 |
| $CH_4$ | 23.1 | 22.0 |
| $C_2H_4$ | 4.6 | 3.8 |
| $C_2H_6$ | 6.5 | 3.7 |
| $C_3H_6$ | 7.9 | 5.6 |
| $C_3H_8$ | 2.0 | 0.8 |
| $C_4$ hydrocarbons | 6.2 | 3.4 |
| $C_5$ hydrocarbons | 4.6 | 2.2 |
| $C_6$ hydrocarbons | 3.2 | 1.4 |
| $C_7$ hydrocarbons | 2.1 | 0.9 |

Table A-continued

| | | |
|---|---|---|
| $C_8$+ hydrocarbons | 0.9 | 0.4 |
| Total CO conversion (mol %) | 97.4 | 89.8 |
| CO conversion to $CO_2$ (mol %) | 16.0 | 22.6 |
| CO conversion to hydrocarbon (mol %) | 81.4 | 67.2 |

[a]Catalyst according to invention
[b]Catalyst using alumina from sodium aluminate process

EXAMPLE 4

A catalyst in accordance with the invention was prepared as described in Example 3 except that 0.23 wt % potassium was employed as promoter. For comparison, another catalyst was similarly prepared using a commercially available alumina derived from a sodium aluminate process (Alcoa A-12) and about 0.24 wt % potassium as promoter.

The two catalysts were compared in Fischer-Tropsch reactions as described in Example 3 with the results tabulated in the following table:

Table B

| Catalyst | 3[a] | 4[b] |
|---|---|---|
| Total Carbon Deposition (wt %) | 17.6 | 15.7 |
| Effluent Composition (wt %) | | |
| CO | 6.0 | 9.4 |
| $CO_2$ | 33.9 | 49.2 |
| $CH_4$ | 31.2 | 17.7 |
| $C_2H_4$ | 4.9 | 4.9 |
| $C_2H_6$ | 4.1 | 1.7 |
| $C_3H_6$ | 7.3 | 5.4 |
| $C_3H_8$ | 1.0 | 0.7 |
| $C_4$ hydrocarbons | 4.4 | 3.7 |
| $C_5$ hydrocarbons | 2.8 | 2.9 |
| $C_6$ hydrocarbons | 2.0 | 2.1 |
| $C_7$ hydrocarbons | 1.6 | 1.5 |
| $C_8$+ hydrocarbons | 0.7 | 0.8 |
| Total CO conversion (mol %) | 95.7 | 92.0 |
| CO conversion to $CO_2$ (mol %) | 15.6 | 26.5 |
| CO conversion to hydrocarbons (mol %) | 80.1 | 65.6 |

[a]Catalyst according to invention
[b]Catalyst using alumina from sodium aluminate process Thus, having described the invention in detail it will be understood by those skilled in the art that certain variations and modifications may be made without departing from the spirit and scope of the invention as described herein and defined in the appended claims.

I claim:

1. A catalyst prepared by a process comprising forming a mixture of magnetite and alumina derived from the water hydrolysis of aluminum alkoxides, said alumina being in the alpha monohydrate or gamma forms and being present in an amount in the range of about 0.01 to 5 weight percent based on the magnetite; calcining the mixture at temperatures in the range of about 650°C to a temperature below that at which the gamma form of alumina is significantly converted to the delta form; and reducing the calcined mixture with a reducing gas at a temperature of about 400° to 475°C until 75 – 80 weight percent of the magnetite is reduced.

2. A catalyst according to claim 1 wherein about 2 to 4 wt %, based on the magnetite, of alumina is present.

3. A catalyst according to claim 2 wherein the magnetite is in the form of mill scale.

4. A catalyst according to claim 2 wherein a promoter selected from the group consisting a silicon salt, silicon dixoide and a salt, oxide, carbonate and hydroxide of an alkali metal and a nonalkali metal, is also employed.

5. A process for preparing a catalyst which comprises forming a mixture of magnetite and alumina derived from the water hydrolysis of aluminum alkoxides, said alumina being in the alpha monohydrate or gamma forms and being present in an amount in the range of about 0.1 to 5 wt % based on the magnetite; calcining the mixture at temperatures in the range of about 650°C to a temperature below that at which the gamma form of alumina is significantly converted to the delta form; and reducing the calcined mixture with a reducing gas at temperatures in the range of 200°C to 600°C until at least 70 wt % of the magnetite is reduced.

6. A process according to claim 5 wherein the amount of alumina employed is in the range of about 2 to 4 wt % based on the magnetite.

7. A process according to claim 5 wherein the mixture is calcined at temperatures in the range of 650°C to 850°C.

8. A process according to claim 7 wherein the mixture is calcined at temperatures in the range of 700°C to 850°C.

9. A process according to claim 7 wherein the calcined mixture is reduced with hydrogen at temperatures in the range of 300°C to 500°C until at least 90 wt % of the magnetite is reduced.

10. A process according to claim 5 wherein the reduced catalyst is preconditioned by passing a gas containing hydrogen and carbon monoxide, the mole ratio of hydrogen to carbon monoxide being at least 3/1, over the catalyst at temperatures in the range of about 200°C to 350°C and pressures in the range of 2 to 30 atmospheres until the catalyst is substantially carbided.

11. A process according to claim 5 wherein a promoter is added to the mixture of magnetite and alumina prior to calcination, wherein said promoter is selected from the group consisting of a salt, oxide, carbonate and hydroxide magnesium, manganese, thorium, cobalt, nickel, titanium, aluminum, copper, and zinc.

12. A process according to claim 5 wherein a promoter selected from the group consisting of a salt, oxide, carbonate and hydroxide of an alkali metal is added to the mixture prior to substantial reduction.

13. A process according to claim 12 wherein the alkali metal is potassium.

14. A process according to claim 10 wherein a promoter is added to the mixture of magnetite and alumina prior to calcination, wherein said promoter is selected from the group consisting of a salt, oxide, carbonate and hydroxide magnesium, manganese, thorium, cobalt, nickel, titanium, aluminum, copper and zinc.

15. A process according to claim 10 wherein promoter selected from the group consisting of a salt, oxide, carbonate and hydroxide of an alkali metal is added to the mixture prior to substantial reduction.

16. A process according to claim 15 wherein the alkali metal is potassium.

* * * * *

UNITED STATES PATENT OFFICE
CERTIFICATE OF CORRECTION

PATENT NO. : 3,965,045
DATED : June 22, 1976
INVENTOR(S) : Bruce E. Leach

It is certified that error appears in the above-identified patent and that said Letters Patent are hereby corrected as shown below:

Column 2, line 1 - delete "lixhed" and insert ---lished---

Column 2, line 10 - delete "catlayst" and insert ---catalyst---

Column 2, line 25 - delete "operatiosn" and insert ---operations---

Column 2, line 29 - delete "but"

Column 3, line 34 - delete "onduct" and insert ---conduct---

Column 3, line 60 - delete "suiable" and insert ---suitable---

Column 5, line 37 - delete "adjuted" and insert ---adjusted---

Column 8, line 38 - delete "65.6" and insert ---65.5---

Column 10, line 8 - after hydroxide insert ---of---

Signed and Sealed this

Twenty-eighth Day of December 1976

[SEAL]

Attest:

RUTH C. MASON
Attesting Officer

C. MARSHALL DANN
Commissioner of Patents and Trademarks